(12) United States Patent
Ciaccia et al.

(10) Patent No.: US 7,204,981 B2
(45) Date of Patent: Apr. 17, 2007

(54) METHODS OF TREATING DISEASES WITH ACTIVATED PROTEIN C

(75) Inventors: Angelina Vucic Ciaccia, Indianapolis, IN (US); Lawrence Mark Gelbert, Indianapolis, IN (US); Brian William Grinnell, Indianapolis, IN (US); Bryan Edward Jones, Carmel, IN (US); David Eugene Joyce, Bloomington, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/221,538

(22) PCT Filed: Mar. 21, 2001

(86) PCT No.: PCT/US01/05823

§ 371 (c)(1),
(2), (4) Date: Sep. 10, 2002

(87) PCT Pub. No.: WO01/72328

PCT Pub. Date: Oct. 4, 2001

(65) Prior Publication Data

US 2003/0073632 A1    Apr. 17, 2003

Related U.S. Application Data

(60) Provisional application No. 60/192,755, filed on Mar. 28, 2000.

(51) Int. Cl.
| | | |
|---|---|---|
| A61K 38/48 | (2006.01) | |
| A61K 38/00 | (2006.01) | |
| C07K 14/435 | (2006.01) | |

(52) U.S. Cl. .................. 424/94.64; 514/2; 530/350; 530/868

(58) Field of Classification Search .......... 424/94.64; 530/350, 868; 514/2
See application file for complete search history.

(56) References Cited

U.S. PATENT DOCUMENTS

| | | | |
|---|---|---|---|
| 4,775,624 A | 10/1988 | Bang et al. | |
| 4,849,403 A | 7/1989 | Stocker et al. | |
| 4,877,608 A | 10/1989 | Lee et al. | |
| 4,981,952 A | 1/1991 | Yan | |
| 4,992,373 A | 2/1991 | Bang et al. | |
| 5,009,889 A * | 4/1991 | Taylor et al. | |
| 5,084,273 A | 1/1992 | Hirahara | |
| 5,093,117 A | 3/1992 | Lawrence et al. | |
| 5,112,949 A | 5/1992 | Vukovich | |
| 5,175,087 A | 12/1992 | Ranby et al. | |
| 5,196,322 A * | 3/1993 | Bang et al. | 435/69.8 |
| 5,254,532 A | 10/1993 | Schwarz et al. | |
| 5,395,923 A | 3/1995 | Bui-Khac et al. | |
| 5,413,732 A | 5/1995 | Buhl et al. | |
| 5,442,064 A | 8/1995 | Pieper et al. | |
| 5,453,373 A | 9/1995 | Gerlitz et al. | |
| 5,478,558 A | 12/1995 | Eibl et al. | |
| 5,516,650 A | 5/1996 | Foster et al. | |
| 5,831,025 A | 11/1998 | Ogata et al. | |
| 5,962,299 A | 10/1999 | Miyata et al. | |
| 6,008,199 A | 12/1999 | Grinnell et al. | |
| 6,037,322 A | 3/2000 | Grinnell et al. | |
| 6,156,734 A | 12/2000 | Grinnell | |
| 6,159,468 A | 12/2000 | Carlson et al. | |
| 6,162,629 A | 12/2000 | Baker et al. | |
| 6,268,337 B1 | 7/2001 | Grinnell | |
| 6,268,344 B1 | 7/2001 | Grinnell | |
| 6,395,270 B1 | 5/2002 | Carlson et al. | |
| 6,426,071 B2 | 7/2002 | Grinnell et al. | |
| 6,436,397 B1 | 8/2002 | Baker et al. | |
| 6,489,296 B1 | 12/2002 | Grinnell | |
| 6,630,137 B1 | 10/2003 | Carlson et al. | |

FOREIGN PATENT DOCUMENTS

| | | |
|---|---|---|
| DE | 3823519 | 1/1990 |
| EP | 0 314 095 | 5/1989 |
| EP | 0 326 014 | 8/1989 |
| EP | 0 357 296 | 8/1989 |
| EP | 0 315 968 | 3/1993 |
| EP | 0 662 513 | 7/1995 |
| EP | 0 726 076 | 8/1996 |
| EP | 0 445 939 | 5/1997 |
| EP | 0 318 201 | 11/1998 |
| JP | 01 226900 | 9/1989 |
| JP | 06 183996 | 7/1994 |
| JP | 07 097335 | 4/1995 |
| JP | 07 165605 | 6/1995 |
| JP | 08 301786 | 11/1996 |

(Continued)

OTHER PUBLICATIONS

Ottesen, LH et al. (1999) Digestive Surgery 16:486-495.*
U.S. Appl. No. 10/635,865, filed Aug. 6, 2003, Carlson et al.
"Anti-inflammatory Therapies to Treat Sepsis and Septic Shock: A Reassessment," *Crit. Care Med.* 25:1095-1100, 1997.
Barbour, et al., "Controversies in Thromboembolic Disease During Pregnancy: A Critical Review," *Obstet. Gynecol.* 86(4) :621-633, 1995.
Bazarbachi, et al., "Changes in Protein C Factor VII and Endothelial Markers After Autologous Bone Marrow Transplantation: Possible Implications in the Pathogensis of Veno-Occlusive Disease," *Nouv Rev Fr Hematol* 35:135-140, 1993.

(Continued)

*Primary Examiner*—Christina Chan
*Assistant Examiner*—F. Pierre Vandervegt
(74) *Attorney, Agent, or Firm*—Lynn D. Apelgren; Danica Hostettler; Brian P Barrett

(57) ABSTRACT

Method of treating a disease or pathological condition with activated protein C or a compound having activated protein C activity by direct regulation of the expression of specific genes associated with the disease or pathological condition.

3 Claims, 2 Drawing Sheets

FOREIGN PATENT DOCUMENTS

| JP | 08 325161 | 12/1996 |
| --- | --- | --- |
| WO | WO 91/12320 | 8/1991 |
| WO | WO 95/11966 | 5/1995 |
| WO | WO 97/20043 | 6/1997 |
| WO | WO 98/48818 | 11/1998 |
| WO | WO 99/20293 | 4/1999 |

OTHER PUBLICATIONS

Blamey, et al., "Protein C Antigen Levels in Major Abdominal Surgery: Relationships to Deep Vein Thrombosis, Malignancy and Treatment with Stanozolol," *Thromb. Haemost.* 54:6223-625, 1985.

Butler, et al., "*Yersinia pestis* Infection in Vietnam. I. Clinical and Hematologic Aspects," *The Journal of Infectious Disease* 129:S78-S84.

Carpenter, et al., "Purpura Fulminans in Pneumococcal Sepsis: Case Report and Review," *Scand J Infec Dis* 29:479-483, 1997.

Chabbat, et al., "The Behavior of Human Activated Protein C in the Plasma of Different Laboratory Animals," *Thromb. Haemost.* 65:A1814, 1991.

Collins, et al., "Factor VIIa and Other Haemostatic Variables Following Bone Marrow Transplantation," *Throm. And Haemo.* 72:28-32, 1994.

Collins, et al., "Pitfalls in Peripheral Vascular Surgery: Disseminated Intravascular Coagulation," *Am. J. Surgery* 124:375-380, 1997.

Conard, et al., "Thrombosis and Pregnancy in Congenital Deficiencies in AT III, Protein C or Protein S: Study of 78 Women," *Throm. Haemost.* 63:319-320, 1990.

Curreri, et al., "Coagulation Dynamics Following Thermal Injury," *Ann. Surg.* 181:161-163, 1974.

Dahlback, et al., "Inherited Thrombophilia: Resistance to Activated Protein C as a Pathogenic Factor of Venous Thromboembolism," *Blood* 85:607-614, 1995.

De Stefano, et al., "Thrombotic Risk During Pregnancy and Puerperium in Women with APC-Resistance—Effective Subcutaneous Heparin Prophylaxis in a Pregnancy Patient," *ThrombHaemost* 74:793-794, 1995.

Esmon, "The Protein C Anticoaglant Pathway," *Arteriosclerosis & Thromb.* 12:135-145, 1992.

Esmon, C.T., "Inflammation: The protein C pathway." *Fibrinolysis & Proteolysis, 11*(Supp 1):143-148 (1997).

Esmon, C.T., "The Regulation of Natural Anticoagulant Pathways" *Science,* 235:1348-1352 (Mar. 1987).

Faioni, et al., "Naturally Occurring Anticoagulants and Bone Marrow Transplantation: Plasma Protein C Predicts the Development of Venocclusive Disease of the Liver," *Blood* 81:3458-3462, 1993.

Fourier, et al., "Septic Shock, Multiple Organ Failure, and Disseminated Intravascular Coagulation," *Chest* 101:816-823, 1992.

Franz, et al., "Clinical Recognition and Management of Patients Exposed to Biological Warfare Agents," *Journal of the American Medical Assoc.* 278(5):399-411, 1997.

Gerson, et al., "Severe Acquired Protein C Deficiency in Purpura Fulminans Associated with Disseminated Intravascular Coagulation: Treatment with Protein C Concentrate," *Pediatrics* 91(2):418-422, 1993.

Gibaldi, "Anatomy of an Antibody, and Related Misadventures in Developing an Effective Treatment for Septic Shock," *Pharmacotherapy* 13(4):302-308, 1993.

Gordon, et al., "Thrombotic Complications of BMT: Association with Protein C Deficiency," *Bone Marrow Transplan.* 11:61-65, 1993.

Graybill, et al., "Complement and Coagulation in Rocky Mountaiin Spotted Fever," *Southern Medical Journal* 66(4):410-413, 1973.

Grey, S.T., et al., "Selective Inhibitory effects of the anticoagulant activated protein C on the responses of human mononuclear phagocytes to LPS, IFN-gamma, or phorbol ester," *Journal of Immunology, 153*(8):3664-3672 (Oct. 15, 1994).

Grinnell, et al., "Trans-Activated Expression of Fully Gamma-Carboxylated Recombinant Human Protein C, An Antithrombotic Factor," *Bio/Technology* 5:1189-1192, 1987.

Gruber, A., et al., "Direct Detection of Activated Protein C in Blood from Human Subjects," *Blood, 79*:2340-2328, 1992.

Haire, et al., "Multiple Organ Dysfunction Syndrome in Bone Marrow Transplantation," *JAMA* 274:1289-1295, 1995.

Harper, et al., "Changes in the Natural Anticoagulants Following Bone Marrow Transplantation," *Bone Marrow Trans.* 5:39-42, 1990.

Harper, et al., "Protein C Deficiency and Portal Thrombosis in Liver Transplantation in Children," *Lancer* 924-927, 1988.

Hill, et al., "Leptospiral Pneumonia," *Seminars in Respiratory Infections* 12(1):44-49, 1997.

Howey, et al., "Preparation for Trials of Recombinant Activated Protein C in Sepsis; A pharmacokinetics and Dynamic Study in Healthy Men and Women," *Chest* 112(3):89S, 1997.

Kercarum, et al., "Apheresis for Severe Malaria Complicated by Cerebral Malaria, Acute Respiratory Distress Syndrome, Acute Renal Failure, and Disseminated Intravascular Coagulation," *Journal of Clinical Apheresis* 7:93-96, 1992.

Koul, et al., "Haemostatic Abnormalities in Multidrug-Resistant Enteric Fever," *Acat Haematol* 93:13-19, 1995.

Koutroubakis, I.E., et al., "Resistance to activated protein C and low levels of free protein S in Greek patients with inflammatory bowel disease," *American Journ. of Gastroenterology, 95*(1):190-194 (2000).

LeClerc, J.R., "Low-Molecular Weight Heparin Prophylaxix in Surgical Patients," *Clin. Appl. Thrombosis/Hemostasis* 3(3):153-156, 1997.

Lercari, et al., "Apheresis for Severe Malaria Complicated by Cerebral Malaria, Acute Respiratory Distress Syndrome, Acute Renal Failure, and Disseminated Intravascular Coagulation," *Journal of Clinical Apheresis* 7:93-96, 1992.

Levi, et al., "Pathogenesis of Disseminated Intravascular Coagulation in Sepsis," *JAMA* 270:975-979, 1993.

Levin, "Syndromes with Renal Failure and Shock," *Pediatric Nephrology* 8:223-229, 1994.

Lo, et al., "Protein C and Protein S Levels in Some Burn Patients," *Burns* 20:186-187, 1994.

Loubser, et al., "Severe Illness caused by *Rickettsia conorii,*" *Annals of Tropical Paediatrics* 13:277-280, 1993.

Maraganore, "Hirudin and Hirulog: Advances in Antithrombotic Therapy," *Perspective in Drug Discovery and Design* 1:461-478, 1994.

Mayer, et al., "Coagulopathies Associated with major Spinal Surgery," *Clin. Orthop.* 245:83-89, 1989.

McManus, et al., "Disseminated Intravascular Coagulation in Burned Patients," *J. of Trauma* 13(5):416-422, 1973.

Menges, et al., "The Role of the Protein C-Thrombomodulin System and Fibrinolysis During Cardiovascular Surgery: Influence of Acute Preoperative Plasmapheresis," *J. Cardiothor. Vasc. An.* 10:482-489, 1996.

Mesters, et al., "Factor VIIa and Antithrombin III Activity During Severe Sepsis and Septic Shock in Neutropenic Patients," *Blood* 88:881-886, 1996.

Murakami, et al., "Activated Protein C Attenuates Endotoxin-Induced Pulmonary Vascular Injury by Inhibiting Activated Leukocytes in Rats," *Blood* 87:642-647, 1996.

Natanson, et al., "Selected Treatment Strategies for Septic Shock Based on Proposed Mechanisms of Pathogenesis," *Ann. Intern. Med.* 120(9):771-783, 1994.

Nguyen, et al., "Varicela and thrombotic complications associated with transient protein C and protein S deficiencies in children," *Eur J Pediatr* 153:646-649, 1994.

Okajima, et al., "Treatment of Patients with Disseminated Intravascular Coagulation by Protein C," *Amer. J. of Hematology* 33:277-278, 1990.

Okajima, K., et al., "Effect of protein C and activated protein C on coagulation and fibrinolysis in normal human subjects," *Thrombosis and Haemostasis* 63(1):48-53, 1990.

Okamoto, et al., Protective/Effect of Neutrophil Elastase Inhibitor (EI) and Activated Protein C (APC) on the Organ Failure and coagulopathy in Cecal Ligation and Puncture (CLP) Sepsis in the Rabbit, *Gastroenterology* 106:A747, 1994.

Ota, "Successful Treatment of Severe Odontogenic Infections which caused Septicemia," *Y.J. Japanese Assoc. Infect. Dis. 68*:157-161, 1994.

Parrillo, "Pathogenetic Mechanisms of Septic Shock," *N. Engl. J. Med. 328*:(20):1471-1477, 1993.

Patent Abstracts of Japan *18*(528) (C-1258), Oct. 6, 1994 (Chemo sero Therapeut Res Inst) Jul. 5, 1994 abstract.

Perry, et al., "Abnormal Hemostasis and Coagulopathy in Preeclampsia and Eclampsia," *Clin. Obstet. Gynecol. 35*:338-350, 1992.

Powars, et al., "Epidemic Meningococcemia and Purpura Fulminans with Induced Protein C Deficiency," *Clin. Infectious Diseases 17*:254-261, 1993.

Puthucheary, et al., "Septicaemic meliodosis: a review of 50 cases from Malaysia," *Transactions of the Royal Society of Tropical Medicine and Hygiene 86*:683-685, 1992.

Pyzh, et al., Database Medline, AN91073823, "Effects of low doses of activated protein C in experimental arterial thrombosis in rats," XP002069505 abstract.

Rathgeber, et al., "Anasthesiologische und Intensivmedizinische Aspekte der Schweren Praeklampsie Mit HELLP-Syndrom," *Anasth Intensivther Notfallmed 25*:206-211, 1990.

Rintala, et al., "Protein C in the Treatment of Coagulopathy in Mengingococcal Disease," *Lancet 347*:1767, 1996.

Rivard, et al., "Treatment of Purpura Fulminans in Meningococcemia with Protein C Concentrate," *J. Pediatr. 126*:646-652, 1995.

S.A. Steiner, et al., Stimulation of the Amidase and Esterase Activity of Activated Bovine Plasma Protein C by Monovalent Cations *Biochemical and Biophysical Research Communications 94*(1):340-347 (May 14, 1980).

Segel, I., "Enzyme Kinetics" (1975) Wiley Interscience, New York, pp. 884-896.

Smith, et al., "Successful Treatment of Meningoccal Induced Protein C Deficiency/Purpura Fulminans in Children with Protein C Concentrate and Heparin," *Thromb. Haemost.* PS1709, p. 419, 1997.

Smith, et al., "Use of Protein C Concentrate, Heparin and Haemodiafiltration in Meningococcus-Induced Purpura Fulminans," *The Lancet 350*:1590-1593, 1997.

Sorenson, et al., "Protein C in Renal Allotransplantation during the Perioperative Period," *J. Inter. Med. 226*:101-105, 1989.

Taylor, et al., "Protein C Prevents the Coagulopathic and Lethal Effects of *Escherichia coli* Infusion in the Baboon.," *J. Clin. Invest. 79*:918-925, 1987.

Taylor, et al., DEGR-Factor Xa Blocks Disseminated Intravascular Coagulation Initiated by *Escherichia coli* without Preventing Shock or Organ Damage, *Blood 78*:364-368, 1991.

Thomas, et al., "Primary Hypercoagulable States in General and Vascular Surgery," *Am. J. Surgery 158*:491-494, 1989.

Ueyama, et al., *Nippon Geka Gakki Zasshi 82*:907-12, 1991.

Uzan, et al., "Elements de Physiopathologie de la Pre-eclampsie et Place des Principaux Examens Complementaires," *Rev. Fr. Gynecol. Obstet. 86*:158-163, 1991.

Veldman, et al., "A New Option in the Treatment of VOD After BMT: Continuous Infusion of Recombinant Tissue Plasminogen Activator and Protein C," *Bone Marrow Trans. 21*:S238, 1988.

Veldman, et al., "Treatment of DIC in Septic Shock with Protein C Concentrate," *Blood 90*:3271, 1997.

Walker, F., "Regulation of Bovine Activated Protein C by Protein S: The Role of the Cofactor Protein in Species Specificity," *Thromb. Res. 22*:321-327, 1981.

Watkins, et al., "The Early Diagnosis of Impending Coagulopathies Following Surgery and Multiple Trauma," *Klin Worchenschr 63*:1019-1027, 1985.

Weinstein, R., et al., "Species Specificity of the Fibrinolytic Effects of Activated Protein C," *Thromb. Res. 63*:123-11, 1991.

Xuhua, H., et al., "Rabbit Plasma, Unlike Its Human Counterpart, Contains no Complex Between Protein S and C4b-Binding Protein," *Thromb. Haemost. 71*:446-451, 1994.

Yu-Chang, J.W. and Hanson, M.A. (1988) "Parenteral formulations of proteins and peptides stability and stabilizers" *Journal of Parenteral Science and Technology 42*(Supp): S3-S26.

Zeffren, et al., "The Study of Enzyme Mechanisms" (1973) John Wiley & Sons, New York, p. 84.

* cited by examiner

| Induced | |
|---|---|
| Gene Description | Accession # |
| Endothelial ENOS | M93718 |
| Human A1 (bcl-2 homologue) | U29680 |
| Human proliferating cell nuclear antigen (PCNA) gene | J05614 |
| Human Gu protein mRNA | U41387 |
| Human IAP homolog B (MIHB) mRNA, complete cds | U37547 |

Fig. 1

| Repressed ||
|---|---|
| Gene Description | Accession # |
| RDC1 | U67784 |
| Human HLA-B null allele mRNA | D49824 |
| Human endothelial leukocyte adhesion molecule 1 (ELAM-1) | M24736 |
| Human vascular cell adhesion molecule 1 | M30257 |
| SOD-2 gene for manganese superoxide dismutase | X65965 |
| Human autoantigen calreticulin mRNA | M84739 |
| Human B61 mRNA | M57730 |
| Human nuclear factor kappa-B2 (NF-KB2) | S76638 U09609 |
| Human major histocompatability complex class I-type DNA | X12432 |
| Human NK4 mRNA, complete cds | M59807 |
| Homo sapiens MAD-3 mRNA encoding lkB-like activity, complete cds | M69043 |
| Human-MHC class I (HLA-A*8001) mRNA | M94880 |
| Human CX3C chemokine precursor, mRNA, alternatively spliced, complete cds | U84487 |
| Human lymphotoxin beta isoform variant, alternatively spliced mRNA, complete cds | U89922 |

Fig. 2

METHODS OF TREATING DISEASES WITH ACTIVATED PROTEIN C

This application claims priority of Provisional Application Ser. No. 60/192,755 filed Mar. 28, 2000.

This invention relates to medical science particularly, utilizing activated protein C for the treatment of diseases or pathological conditions associated with specific gene induction or repression.

Protein C is a serine protease and naturally occurring anticoagulant that plays a role in the regulation of vascular hemostasis by inactivating Factors Va and VIIIa in the coagulation cascade. Human protein C is made in vivo primarily in the liver as a single polypeptide of 461 amino acids. This precursor molecule undergoes multiple post-translational modifications to produce circulating 2-chain zymogen that is activated in vivo by thrombin in complex with thrombomodulin at a phospholipid surface in the presence of calcium ion. Activation results from removal of a dodecapeptide at the N-terminus of the heavy chain, producing activated protein C (aPC).

In conjunction with other proteins, aPC functions as perhaps the most important down-regulator of blood coagulation, resulting in protection against thrombosis. In addition to its anti-coagulation functions, aPC has anti-inflammatory effects through its inhibition of cytokine generation (e.g. TNF and IL-1) and also possesses profibrinolytic properties that facilitate clot lysis. Thus, the protein C enzyme system represents a major physiological mechanism of anti-coagulation, anti-inflammation, and fibrinolysis.

The mechanism(s) by which protein C exerts its various activities has been an active area of research for many years. It is known that protein C binds to the endothelial protein C receptor (EPCR). This interaction facilitates more efficient activation of protein C by thrombin and propagation of the anticoagulant response (Stearns-Kurosawa, et al. *Blood*, 94(10):2878, 1999). It has also been postulated that the anti-inflammatory activity of protein C is related, in part, to the interaction of the oligosaccharide portion of the protein with selectins (Yan, et al., *Glycobiology* (3) 957–608, 1993). Moreover, aPC has been shown to have direct anti-inflammatory effects on monocytes. Furthermore, data suggest that activated protein C exhibits its profibrinolytic effects either by stimulation of the release of plasminogen activators into the blood and/or by neutralization of plasminogen activator inhibitor (PAI-1) (Castellino, F. J., *Trends in Cardiovasc Med* (5) 55–62, 1995) and by reduced generation of thrombin activated fibrinolysis inhibitor [TAFI] (Nesheim et al., *Throm. and Haem.*, 78(1):386–391, 1997)

However, the effect of protein C at the molecular level has not been elucidated. Therefore, there is a need in the art to discover the direct effect of protein C on the induction or repression of genes associated with various disease states or pathological conditions. Thus, the elucidation of such protein C regulated genes provides useful and valuable information leading to new therapeutic treatments for aPC.

In one embodiment of the invention, a method is provided for treating a disease or pathological condition associated with apoptotic cell death which comprises administering a pharmaceutically effective amount of activated protein C or a compound having activated protein C activity.

Another aspect of the invention is a method of increasing the activity of Bcl-2 in cells affected by a disease or pathological condition associated with apoptosis which comprises administering a pharmaceutically effective amount of activated protein C or a compound having activated protein C activity.

Another embodiment of the invention is a method of increasing the activity of human IAP homolog B in cells affected by a disease or pathological condition associated with apoptosis which comprises administering a pharmaceutically effective amount of activated protein C or a compound having activated protein C activity.

Yet another embodiment of the invention is a method of treating a patient suffering from a disease or pathological condition induced by NF-kB which comprises administering a pharmaceutically effective amount of activated protein C or a compound having activated protein C activity.

Yet another aspect of the invention provides a method of treating a disease or pathological condition where TNF-α is a primary modulator of pathophysiology which comprises administering a pharmaceutically effective amount of activated protein C or a compound having activated protein C activity.

Another aspect of the invention provides a method for treating a disease of pathological condition where PCNA or Gu protein is a regulator of cell growth and survival which comprises administering a pharmaceutically effective amount of activated protein C or a compound having activated protein C activity.

In yet another aspect of the invention a method is provided for treating a disease or pathological condition where cell-cell adhesion is a modulator of pathophysiology which comprises administering a pharmaceutically effective amount of activated protein C or a compound having activated protein C activity.

Another embodiment of the invention provides for the use of activated protein C or a compound having activated protein C activity in the manufacture of a medicament for the treatment of a disease or pathological condition associated with apoptotic cell death.

Yet another embodiment of the invention provides for the use of activated protein C or a compound having activated protein C activity in the manufacture of a medicament for the treatment of a disease or pathological condition where TNF-α is a primary modulator of pathophysiology; where PCNA or Gu protein is a regulator of cell growth and survival; where cell-cell adhesion is a modulator of pathophysiology; and, where a disease or pathological condition is induced by NF-kB.

It is contemplated that the activated protein C as indicated for the above treatments is human activated protein C.

In another embodiment, a method is provided for screening to identify test substances that induce or repress expression of genes that are induced or repressed by activated protein C. The level of expression of an RNA transcript or its translation product in a first sample is compared to the level of expression induced by activated protein C. The level of expression of an RNA transcript or its translation product in a second sample is compared to the level of expression repressed by activated protein C.

In another aspect of the invention a method is provided for screening to identify test substances which modulate the activity of activated protein C on the induction or repression of genes. A cell is contacted with a test substance in combination with activated protein C and the level of expression of an RNA transcript or its translation product in a first sample is compared to the level of expression induced by activated protein C alone. A cell is contacted with a test substance in combination with activated protein C and the level of expression of an RNA transcript or its translation product in a second sample is compared to the level of expression repressed by activated protein C alone.

The first sample in the above embodiments is a transcript of a gene selected from the group consisting of gene numbers 1–5 as shown in FIG. 1. The second sample in the above embodiments is a transcript of a gene selected from the group consisting of gene numbers 1–15 as shown in FIG. 2.

FIG. 1 is a Table showing genes induced by activated protein C.

FIG. 2 is a Table showing genes repressed by activated protein C.

For purposes of the present invention, as disclosed and claimed herein, the following terms are as defined below.

aPC or activated protein C refers to recombinant activated protein C (rhAPC). Preferably aPC is human protein C (ZOVANT™, recombinant human activated protein C, Eli Lilly & Co.) or derivatives having proteolytic, amidolytic, esterolytic, and biological (anticoagulant, anti-inflammatory, or pro-fibrinolytic) activities characteristic of human aPC. Examples of protein C derivatives are described by Gerlitz, et al., U.S. Pat. No. 5,453,373, and Foster, et al., U.S. Pat. No. 5,516,650, the entire teachings of which are hereby incorporated by reference. Recombinant activated protein C may be produced by activating recombinant human protein C zymogen in vitro or by direct secretion from cells of the activated form of protein C. Protein C may be produced in transgenic animals, transgenic plants, or in a variety of eukaryotic cells, including, for example, secretion from human kidney 293 cells as a zymogen then purified and activated by techniques known to the skilled artisan.

Treating—describes the management and care of a patient for the purpose of combating a disease, condition, or disorder whether to eliminate the disease, condition, or disorder, or prophylactically to prevent the onset of the symptoms or complications of the disease, pathological condition, or disorder.

Continuous infusion—continuing substantially uninterrupted the introduction of a solution or suspension into a vein for a specified period of time.

Bolus injection—the injection of a drug in a defined quantity (called a bolus) over a period of time up to about 120 minutes.

Suitable for administration—a lyophilized formulation or solution that is appropriate to be given as a therapeutic agent.

Hypercoagulable states—excessive coagulability associated with disseminated intravascular coagulation, pre-thrombotic conditions, activation of coagulation, or congenital or acquired deficiency of clotting factors such as aPC.

Zymogen—protein C zymogen, as used herein, refers to secreted, inactive forms, whether one chain or two chains, of protein C.

Pharmaceutically effective amount—a therapeutically efficacious amount of a pharmaceutical compound. The particular dose of the compound administered according to this invention will, of course, be determined by the attending physician evaluating the particular circumstances surrounding the case, including the compound administered, the particular condition being treated, the patient characteristics and similar considerations.

It is the discovery of the present invention that activated protein C modulates a whole host of genes, increasing and decreasing expression of their mRNA and protein products. These genes have not previously been identified as being modulated by activated protein C. The now-established modulation by activated protein C indicates that the genes are involved in the progression or inhibition of various disease states or pathological conditions. Furthermore, the present invention also describes the method of treating diseases or pathological conditions associated with the modulation of the identified genes.

The modulation of the indicated genes was determined by transcriptional profiling which is the simultaneous monitoring of gene expression for a large part of an organism's genome. Analysis of transcriptional profiles provides information underlying molecular basis of cellular development and differentiation, identifies biological and signal transduction pathways, determines genes that are coordinately expressed, identifies the function of novel genes, and provides insights into the pathophysiology of diseases (Lander, E. S. *Science* 274:536–539, 1996; Lander, E. S. *Nat. Genet.*, 21(Suppl):3–4, 1999; Lockhart, et al., *Nature Genetics* 21(Suppl): 20–24, 1999)

A sampling of 6800 human genes were tested for the effects of activated protein C on their expression. Such a comprehensive and unbiased screening permits the identification of many genes which were heretofore not known to be modulated by activated protein C.

The level of expression of an RNA transcript or its translation product (protein) can be determined using any techniques known in the art. Specific oligonucleotide probes for the relevant genes can be used in hybridization experiments, as is known in the art. Any hybridization format for determining RNA levels can be used, including but not limited to cDNA microarrays, RT-PCR, subtractive hybridization, Northern blots, slot blots, dot blots, and hybridization to oligonucleotide arrays. Specificity of hybridization can be assessed by varying degrees of stringency of the hybridization conditions. In addition, comparison of mismatch to perfect match oligonucleotide probes can be used to determine specificity of binding. To assess specific translation product expression levels, antibodies specific for the protein can be used readily. Again, any format known in the art for measuring specific protein levels can be used, including sandwich assays, ELISAs, immunoprecipitations, and Western blots. Any of monoclonal antibodies, polyclonal antibodies, single chain antibodies, and antibody fragments may be used in such assays. Specificity of immunologic reactions can be assessed using competitor antibodies or proteins, as well as varying the immunoreaction conditions. Monitoring expression product levels involves determining amounts of a specific expression product. Amounts determined need not be absolute amounts, but may be relative amounts determined under different conditions, for example, in the presence and absence of a test compound.

Probes according to the present invention may be labeled or unlabeled, tethered to another substance or in solution, synthetically made or isolated from nature. Probes can be nucleic acids, either RNA or DNA, which contain naturally occurring nucleotide bases or modified bases. The probes may contain normal nucleotide bonds or peptide bonds. Oligonucleotide probes may be of any length which provides meaningful specificity of hybridization. Thus probes may be as small as 10 nucleotides, and preferably they are between 12 and 30 nucleotides in length. However, oligonucleotide probes may be significantly longer, in the range of 30 to 100 nucleotides, 100 to 500 nucleotides or 500 to 2000 nucleotides. Probes may be attached to polymers, either soluble or non-soluble. Probes may be attached or bonded to solid substrates such as filters, sheets, chips, slides, and beads.

High density arrays are particularly useful for monitoring the expression control at the transcriptional, RNA processing and degradation level (transcriptional profiling). The fabrication and application of high density arrays in gene expression monitoring have been disclosed previously in, for example, U.S. Pat. No. 6,020,135 incorporated herein by reference. Each oligonucleotide occupies a known location on a substrate. A nucleic acid target sample is hybridized with a high density array of oligonucleotides and then the amount of target nucleic acids hybridized to each probe in the array is quantified. One preferred quantifying method is to use confocal microscope and fluorescent labels. The GeneChip® system (Affymetrix, Santa Clara, Calif.) is particularly suitable for quantifying the hybridization; however, it will be apparent to those of skill in the art that any similar systems or other effectively equivalent detection methods can also be used.

A variety of primary mammalian cell lines may be utilized for transcriptional profiling to analyze the effect of activated protein C on the modulation of specific genes. Such mammalian cell lines may include, but are not limited to: peripheral blood leukocytes, bone marrow cells, endothelial cells, pulmonary epithelial cells, pulmonary macrophages, intestinal epithelium, keratinocytes, neuronal cell populations, synovial cells, liver cells, kidney cells, spleen-derived cell populations, osteoblasts, osteoclasts, smooth muscle cells, myocytes (skeletal and cardiac) dendritic cells, or prostate cells. In the present invention, transcriptional profiling was used to analyze how aPC modulates the inflammatory response in endothelial cells. RNA was isolated from human umbilical vein endothelial cells (HUVEC), HUVEC treated with aPC, HUVEC treated with tumor necrosis factor $\alpha$(TNF-$\alpha$) to induce a state of cell activation or mimic an inflammatory response, and HUVEC treated with aPC plus TNF-$\alpha$.

Genes whose transcription was induced by activated protein C are shown in FIG. 1. Similarly, genes whose transcription was repressed by activated protein C are shown in FIG. 2 and in Example 2.

Activated protein C induces the gene expression of human Al (bcl-2 homologue) and human IAP homolog B (MIHB), FIG. 1 and Example 1. The bcl-2 family members inhibit most types of apoptotic cell death and is thought to function by regulating an antioxidant pathway at sites of free radical generation (Hockenbery et al. Cell 75:241–251, 1993). Apoptosis is the term used to describe a type of cellular death that occurs in many tissues as a normal physiological process. Also called "programmed cell death," this form of cellular demise involves the activation in cells of a built-in genetic program for cell suicide by which cells essentially autodigest. An aspect of the present invention is the inhibition of apoptosis by activated protein C. This has been exemplified in several cell types as shown in Example 3.

In contrast to the effect of apoptosis in normal cellular phenomenon, when aberrantly regulated, the death of cells through apoptosis can lead to a variety of disease states and pathological conditions. For example, the death of neurons that occurs in diseases such as Alzheimer's dementia and Parkinson's disease shows many hallmarks of apoptosis. Autoimmune diseases, where immune cells inappropriately attack normal tissues, is due, in part, to a failure of apoptosis to occur. Additionally, cell death caused by viral infection can occur through apoptosis in many cases, including T-cell death induced by the Human Immunodeficiency Virus (HIV) that causes AIDS.

MIHB is a homolog of IAP which is an inhibitory apoptosis protein. Therefore the induction of bcl-2 and/or MH1B will inhibit apoptosis which in turn will inhibit diseases or pathological conditions associated with apoptosis. Thus activated protein C by inducing the gene expression of bcl-2 and/or MH1B is useful for treating diseases or pathological conditions associated with apoptosis. Preferred diseases or pathological conditions associated with apoptosis that activated protein C is useful in treating are rheumatoid arthritis, inflammatory bowel disease, vasculitis, ischemic renal failure, insulin-dependent diabetes mellitus, pancreatis, psoriasis, multiple sclerosis, Hashimoto's thyroiditis, Graves disease, systemic lupus erythematosus, autoimmune gastritis, fibrosing lung disease, HIV-induced lymphoma, fulminant viral hepatitis B, fulminant viral hepatitis C, chronic hepatitis, chronic cirrhosis, H. pylori-associated ulceration, atherosclerosis, cytoprotection during cancer treatment, chronic glomeruonephritis, osteoporosis, aplastic anemia, myelodysplasia, Alzheimer's disease, Parkinson's disease. Activated protein C induces the gene expression of human proliferating cell nuclear antigen (PCNA) and human Gu protein, FIG. 1 and Example 1. Proliferating cell nuclear antigen (PCNA) plays an essential role in nucleic acid metabolism as a component of the replication and repair machinery. One of the well-established functions for PCNA is its role as the processivity factor for DNA polymerase $\delta$ and $\epsilon$. PCNA tethers the polymerase catalytic unit to the DNA template for rapid and processive DNA synthesis and thus is associated with cell growth and survival. The Gu protein is a member of a new subgroup of RNA helicases and has been associated with cell growth and survival. Therefore, activated protein C is useful for treating a disease or pathological condition where PCNA or Gu protein is a regulator of cell growth and survival. Examples of such regulation include, but is not limited to, regulation of cell growth on endothelial cells and increasing angiogenesis, which is necessary in wound healing and for restoring blood flow to tissues after injury or insult.

Activated protein C induces the gene expression of endothelial nitric oxide synthase (ENOS), FIG. 1. ENOS is involved in controlling platelet function both in vitro and in vivo. Platelet haemostasis is maintained by the release of ENOS from the endothelium, endocardium and the platelets themselves. ENOS generated in this system inhibits platelet adhesion and aggregation and promotes disaggregation of preformed platelet aggregates. In addition, ENOS has been associated with relaxation of smooth muscle.

The inhibitory activity of ENOS is due largely to its interaction with the soluble guanylate cyclase and the resultant increase in cGMP. The subsequent cGMP-mediated reactions are less clear, but they lead to the inhibition of the expression of the platelet glycoproteins, including IIb/IIIa and P-selectin. Decreased generation of endothelial ENOS has been associated with a deleterious effect on the integrity of vessel walls due to endothelial cell activation and platelet adhesion. Thus activated protein C by inducing the gene expression of endothelial ENOS is useful for treating diseases or pathological conditions due to endothelial cell activation and platelet adhesion. Examples of such diseases include, but are not limited to, coronary artery atheroscleosis, arterial restenosis following balloon angioplasty, hypertension, cardiac failure, coronary disease after transplantation, and pregnancy-induced hypertension and preeclampsia.

Unexpectedly, activated protein C repressed the expression of the gene for nuclear factor kappa B (NF-kB), FIG. 2. NF-kB is a transcriptional factor activated by a wide variety of agents including the inflammatory cytokines IL-1, and TNF. As a transcription factor, NF-kB regulates the expression of genes involved in immune cell activation, B and T cell development, anti-viral and anti-microbial responses.

The ability of aPC to inhibit NF-kB mediated effects is useful for treating diseases or pathological conditions where NF-kB is induced. Examples of specific diseases or pathological conditions associated with the induction of NF-kB include, but are not limited to, neuronal degeneration diseases, graft versus host reactions, acute inflammatory conditions, systemic inflammatory responses, acute phase response, ischemic reperfusion injury, atherosclerosis, HIV infection, and cancer.

The effects of TNF-α as an inflammatory cytokine are well known in the art. The ability of aPC to inhibit TNF-α mediated effects, as shown in FIG. 2 and in Example 1, is useful for treating diseases or pathological conditions where TNF-α is a primary modulator of pathophysiology. Examples of specific diseases or pathological conditions associated with the induction of TNF-α include, but are not limited to, Crohn's disease, ulcerating colitis, arthritis, acute peritoneal inflammation, and heart failure.

Activated protein C suppressed TNF-α induction of MHC class 1 genes, FIG. 2. In all vertebrates there is a genetic region that has a major influence on graft survival. This region is referred to as the Major Histocompatibility Complex (MHC). Individuals identical for this region can exchange grafts more successfully than MHC non-identical combinations. The MHC products play an important role in antigen recognition by T cells. Therefore, aPC is useful in treating diseases or pathological conditions where MCH class 1 or HLA-B null allele are modulators of immune function. Examples of such diseases or pathological conditions include, but are not limited to, organ transplantation, infectious disease, or autoimmune disease.

Activated protein C repressed the transcription of B61 and lymphotoxin beta isoform variant, FIG. 2. The products of these genes are pro-inflammatory cytokines. Thus, activated protein C is useful for treating diseases or pathological conditions that are inflammatory in nature. Examples of such diseases or pathological conditions include, but are not limited to, acute inflammatory conditions, systemic inflammatory responses, acute phase response, and acute peritoneal inflammation.

Activated protein C repressed the transcription of ELAM-1, VCAM-1, PECAM-1, and human CX3C chemokine precursor, FIG. 2 and Example 2. The products of these genes are involved in cell-cell adhesion and cell-cell interaction. Thus, activated protein C is useful for treating diseases or pathological conditions where cell-cell adhesion is a modulator of pathophysiology.

Activated protein C repressed the transcription of calreticulin, FIG. 2. Auto-antibodies to calreticulin have been associated with numerous autoimmune disorders. It follows therefore, that decreasing the amount of calreticulin by transcriptional repression will in turn result in fewer auto-antibodies being produced. Thus, activated protein C is useful for treating diseases or pathological conditions where anti-calreticulin antibodies are a modulator of pathophysiology. Examples of such diseases or pathological conditions are, but are not limited to, systemic lupus erythematosus, Sjogren's syndrome, onchocerciasis, rheumatoid arthritis, mixed connective tissue disease, and complete congenital heart block.

Activated protein C repressed the transcription of thrombospondin (TSP-1), Example 2. TSP-1 is an extracellular matrix glycoprotein that is synthesized and secreted by a variety of cell types, including endothelial and tumor cells. TSP-1 released by activate platelets participates in the formation of molecular bridges between platelets and leukocytes that are recruited as part of the inflammatory process. TSP-1 also regulates angiogenesis through its effect on the adhesion and proliferation of endothelial cells and is thought to play a role in the progression of tumors. TSP-1 is an activator of TGF-β, a cytokine involved in cell growth, differentiation, and immune modulation. Induction of TGF-β is associated with kidney fibrosis and cardiac hypertrophy following myocardial infarction. Thus, activated protein C is useful for treating diseases or pathological conditions associated with elevated levels of TSP-1 and TGF-β. Examples of such diseases or pathological conditions include, but are not limited to, breast cancer, GI malignancies, gynecological cancers, lung cancer, kidney fibrosis and cardiac hypertrophy following myocardial infarction.

Activated protein C represses the transcription of RDC1, FIG. 2. RDC1 is related to the family of proteins known as G-protein coupled receptors. It is well established that many significant biological processes are mediated by participating in signal transduction pathways that involve G-proteins. Therefore, activated protein C is useful for treating diseases or pathological conditions associated with elevated levels of RDC1. Examples of such diseases or pathological conditions include, but are not limited to, bacterial, fungal, protozoan and viral infections, particularly infections caused by HIV-1 or HIV-2; pain; cancers; anorexia; bulimia; asthma; Parkinson's disease; acute heart failure; hypotension; hypertension; urinary retention; osteoporosis; angina pectoris; ulcers; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

In another embodiment of the present invention, a method is provided for screening to identify compounds or test substances that induce or repress expression of genes that are induced or repressed by activated protein C. The level of expression of an RNA transcripts or its translation product in a first sample is compared to the level of expression induced by activated protein C. The level of expression of an RNA transcript or its translation product in a second sample is compared to the level of expression repressed by activated protein C.

The preferred cell type for the above embodiment is the endothelial cell although other cell types may be considered and are contemplated by the present invention. The first sample in the above embodiment is a gene transcript of one or more genes, preferably 2 to 5 genes, most preferably 5 genes, selected from the group consisting of the genes described in FIG. 1. The second sample in the above embodiment is a gene transcript of one or more genes, preferably 2 to 14 genes, even more preferably 7 to 14 genes, most preferably 14 genes, selected from the group consisting of the genes described in FIG. 2.

In another aspect of the invention a method is provided for screening to identify test substances which modulate the activity of activated protein C on the induction or repression of genes. A cell is contacted with a test substance in combination with activated protein C and the level of expression of an RNA transcript or its translation product in a first sample is compared to the level of expression induced by activated protein C alone.

A cell is contacted with a test substance in combination with activated protein C and the level of expression of an RNA transcript or its translation product in a second sample is compared to the level of expression repressed by activated protein C alone.

The preferred cell type for the above embodiment is the endothelial cell although other cell types may be considered and are contemplated by the present invention. The first sample in the above embodiment is a gene transcript of one or more genes, preferably 2 to 5 genes, most preferably 5 genes selected from the group consisting of the genes described in FIG. 1. The second sample in the above embodiment is a gene transcript of one or more genes, preferably 2 to 14 genes, even more preferably 7 to 14 genes, most preferably 14 genes, selected from the group consisting of the genes described in FIG. 2.

Compounds identified in one or more of the above screens would have activated protein C activity or would modulate protein C activity and would be useful to treat diseases or pathological conditions that are effectively treated with activated protein C as described herein. The identified compounds may be administered alone or in combination with activated protein C. The phrase "in combination with" refers to the administration of a compound with activated protein C, either simultaneously, sequentially, or a combination thereof.

Protein C can be formulated according to known methods to prepare a pharmaceutical composition comprising as the active agent, aPC, and a pharmaceutically acceptable solid or carrier. For example, a desired formulation would be one that is a stable lyophilized product of high purity comprising a bulking agent such as sucrose, a salt such as sodium chloride, a buffer such as sodium citrate and activated human protein C. A preferred stable lyophilized formulation comprises a weight ratio of about 1 part activated protein C, between 7 to 8 parts salt and between about 5 and 7 parts bulking agent. Examples of stable lyophilized formulations include: 5.0 mg/ml activated protein C, 30 mg/ml sucrose, 38 mg/ml NaCl and 7.56 mg/vial citrate, pH 6.0; and, 20 mg/vial activated protein C, 120 mg/ml sucrose, 152 mg/vial NaCl, 30.2 mg/vial citrate, pH 6.0.

Preferably, protein C will be administered parenterally to ensure delivery into the bloodstream in an effective form by injecting a dose of 0.01 mg/kg/day to about 10.0 mg/kg/day, B.I.D. (2 times a day), for one to ten days. More preferably, the protein C will be administered B.I.D. for three days.

Alternatively, the protein C will be administered as a continuous infusion for 1 to 240 hours. More preferably, the protein C will be administered as a continuous infusion for 1 to 196 hours. Even more preferably, the protein C will be administered as a continuous infusion for 1 to 144 hours. Yet even more preferably, the protein C will be administered as a continuous infusion for 1 to 96 hours.

The amount of protein C administered by continuous infusion will be from about 0.01 µg/kg/hr to about 50 µg/kg/hr. More preferably, the amount of human protein C derivative administered will be about 0.1 µg/kg/hr to about 40 µg/kg/hr. Even more preferably the amount of protein C administered will be about 1 µg/kg/hr to about 30 µg/kg/hr. The most preferable amounts of protein C administered will be about 24 µg/kg/hr.

The preferred plasma ranges obtained from the amount of protein C administered will be 0.02 ng/ml to less than 100 ng/ml. More preferred plasma ranges are from about 0.2 ng/ml to 50 ng/ml. Most preferred plasma ranges are from about 2 ng/ml to about 60 ng/ml and still more preferred about 40 ng/ml to about 50 ng/ml.

In another alternative, protein C will be administered by injecting a portion (⅓ to ½) of the appropriate dose per hour as a bolus injection over a time from about 5 minutes to about 120 minutes, followed by continuous infusion of the appropriate dose for up to 240 hours.

In another alternative, the protein C will be administered by local delivery through an intracoronary catheter as an adjunct to high-risk angioplasty (with and without stenting, and with or without combination antithrombotic therapy with or without anti-platelet agents). The amount of protein C administered will be from about 0.01 mg/kg/day to about 10.0 mg/kg/day by continuous infusion, bolus injection, or a combination thereof.

In anther alternative, aPC will be injected directly into the joints.

In yet another alternative, protein C will be administered subcutaneously at a dose of 0.01 mg/kg/day to about 10.0 mg/kg/day, to ensure a slower release into the bloodstream. Formulation for subcutaneous preparations will be done using known methods to prepare such pharmaceutical compositions.

The following Examples are provided merely to further illustrate the present invention. The scope of the invention shall not be construed as merely consisting of the following Examples.

Preparation 1

Preparation of Human Protein C

Recombinant human protein C (r-hPC) was produced in Human Kidney 293 cells by techniques well known to the skilled artisan such as those set forth in Yan, U.S. Pat. No. 4,981,952, Bang, et al., U.S. Pat. Nos. 4,775,624 and No. 4,992,373, and in Grinnell, et al., 1987, *Bio/Technology* 5:1189–1192 the entire teachings of which are herein incorporated by reference.

Recombinant human protein C (r-hPC) was activated by methods well known in the art. Specifically, r-hPC was activated with bovine thrombin as described in Carlson, et al., U.S. Pat. No. 6,159,468, herein incorporated by reference.

EXAMPLE 1

Modulation of Markers of Apoptosis by Recombinant Human Activated Protein C

Transcriptional profiling using Affymetrix DNA chip technology was used to analyzed how aPC modulates genes associated with apoptosis using primary human endothelial cells. RNA was isolated from Human Umbilican Vein Endothelial (HUVEC) cells and HUVEC treated with aPC as follows. Pooled HUVEC P096 cells were obtained as first passage from Clonetics (catalog #CC-2519, lot #6F0081) and cultured in Clonetics EBM basal medium supplemented with 2% fetal bovine serum, 12 µg/ml gentamicin, and 50 ng/ml amphotericin-B (Clonetics EGM BulletKit, catalog #CC3124). The cells were passaged three times and then grown to approximately 80–90% confluence in 60 ml medium prior to treatment. The medium was changed approximately six hours prior to treatment. Fifty two T225 flasks were divided into four treatment groups of thirteen flasks each; control, aPC, TNF-α, and APC +TNF-α. The cells were treated with 183 nM recombinant human aPC (Lilly lot #PPD02890) or an equal volume of vehicle (20 mM Tris, pH 7.5, 150 mM NaCl) for nine hours, or 1 ng/ml TNF-α (R & D Systems) or an equal volume of vehicle (0.1% BSA in PBS) for seven hours. The cells were washed once with PBS and then dislodged by treatment with trypsin (6 ml 0.025% trypsin/EDTA per flask for 5 minutes.) After inhibiting the trypsin with 6 ml of Trypsin Neutralizing Solution, the cells were spun for five minutes at 1000 rpm. The cell pellets were kept on ice for a maximum of thirty minutes until resuspension in Trizol (10 ml total Trizol per 13 flasks of each condition). The poly (A) RNA was isolated by conventional procedures, and was labeled and hybridized to oligonucleotide arrays allowing for the analysis of gene expression. The experiment was performed in duplicate. The resulting data was analyzed using commercially available software (GeneChip, Affymetrix). Reverse transcription PCR (RT-PCR) was used to confirm the initial observations from the Gene chips. As shown in Table, both the anti-apoptotic factor Bcl-2 and the marker PCNA were found to be up-regulated by treatment of HUVECs with APC.

TABLE 1

Modulation of genes associated with cell survival and apoptosis
Relative level of Expression

|  | PCNA | GU | IAP | Bcl-2 |
|---|---|---|---|---|
| Untreated | 1 | 1 | 1 | 1 |
| APC-treated | 2.8 | 5.1 | 1.8 | 2 |

We also observed genes that were suppressed by aPC including the B6 gene, an immediate-early response gene of endothelium that has been suggested to participate in mediating the response of the vascular endothelium to proinflammatory cytokines (Holzman et al, 1990, MCB 10:5830). We observed a significant suppression as evidenced by loss of detectable mRNA signal following aPC treatment (Table 2). In contrast, TNF-treated cells as a control for gene response, showed an 11-fold increase in B-6.

TABLE 2

Modulation of B-6 gene associated with proinflammatory response
Relative Level of Expression

| Untreated | 1 |
|---|---|
| TNF Treated (control) | 11.3 |
| APC Treated | Below detectable limits |

EXAMPLE 2

Identification of Genes Modulated by Activated Protein C Using Subtractive Hybridization Subtractive hybridization is a powerful technique that enables researchers to compare two populations of mRNA and obtain clones of genes that are expressed in one population but not in the other. Subtractive hybridization was used to identify genes that are up-regulated or down-regulated by activated protein C. HUVEC cells were treated with aPC as described in Example 1. The poly (A) RNA was isolated from cells by conventional techniques and used to construct reverse (library of genes down-regulated by aPC) and forward (library of genes up-regulated by aPC) subtracted cDNA libraries using a commercially available kit (Clontech PCR-Select cDNA Subtraction Kit). Several genes were identified as being differentially expressed in the reverse-subtracted library, including but not limited to thrombospondin-1 and PECAM-1. The down-regulation of these genes by aPC was validated using standard RT-PCR analysis of the original RNA isolated for control and aPC-treated HUVECs. The down regulation of these genes by aPC was confirmed by Western blot and flow cytometry analysis.

EXAMPLE 3

Inhibition of Apoptosis by rhAPC

The inhibition of apoptosis by rhAPC in primary human umbilical venous endothelial cells (HUVEC) or the immortalized endothelial cell line (Eahy926) is shown below utilizing the APOPercentage™ Apoptosis Assay. The APOPercentage™ Apoptosis Assay is done per manufacturer's instructions (Biocolor Ltd., Belfast, N. Ireland). Briefly, adherent cells (HUVEC, Eahy926, or 293) are seeded at $3 \times 10^4$ cells per well and treated with staurosporine, 1 ug/ml (Sigma, St. Louis, Mo.), for one hour or with staurosporine and rhAPC (pretreatment 16 hours). Staurosporine is an alkaloid isolated from the culture broth of *Streptomyces staurospores* and a potent inhibitor of protein kinase C and inducer of apoptosis.

Cells are prepared and stained per manufacturer's instructions. Significant inhibition of apoptosis by rhAPC is observed in both the HUVEC (Table 3) and Eahy926 (Table 4) endothelial cell lines.

TABLE 3

Apoptosis Inhibition in HUVEC Cells

| Treatment | Percent Apoptosis | Std. Error |
|---|---|---|
| Untreated | 16.3 | 2.1 |
| Staurosporine 1 uM | 100.0 | 1.61 |
| Staurosporine + rhAPC 0.5 ug/ml | 59.0 | 16.7 |

TABLE 4

Apoptosis Inhibition EAhy926 Cells

| Treatment | Percent Apoptosis | Std. Error |
|---|---|---|
| Untreated | 20.0 | 0053 |
| Staurosporine 1 uM | 100 | 3.3 |
| Staurosporine + rhAPC 0.5 ug/ml | 21.0 | 0.41 |

The inhibition of apoptosis by rhAPC in U937 monocytes utilizing the Caspase-3 intracellular staining assay is shown in Table 5.

The Caspase-3 intracellular staining is run as follows. U937 cells are grown to $1 \times 10^6$ cells per ml. The cells are pretreated with rhAPC for 16 hours. Staurosporine 1 ug/ml is then added for 3 hours. The cells are washed in HBSS, calcium and magnesium free, pelleted and washed with PBS/albumin 1% with Na Azide 0.02%. The cells are then fixed and permeabilized with the Cytofix/Cytoperm™ Kit (PharMingen/BD, San Diego, Calif. Intracellular staining with anti-active caspase-3 (PharMingen/BD, San Diego, Calif.) at 10 uL per $1 \times 10^6$ cells is for 30 minutes at 4 degrees Celsius. Cells are pelleted, resuspended in PBS/albumin buffer $2 \times 10^6$ cells/ml and analyzed with a Coulter Flow Cytometer (Coulter™). Significant inhibition of apoptosis by rhAPC is observed in the U937 cell line.

TABLE 5

Apoptosis Percentage Inhibition in U937 Cells Caspase-3 Assay

| rhAPC ug/ml | % Apoptosis | Std Error |
|---|---|---|
| 0 | 100 | 2.06 |
| 0.1 | 22.5 | 0.41 |

TABLE 5-continued

Apoptosis Percentage Inhibition in U937 Cells Caspase-3 Assay

| rhAPC ug/ml | % Apoptosis | Std Error |
|---|---|---|
| 1.0 | 18.8 | 0.04 |
| 5.0 | 21.9 | 0.12 |

The inhibition of apoptosis by rhAPC in U937 cells and 293 cells utilizing the Annexin V assay is shown in Tables 6 and 7 respectively. The Annexin V staining assay is done as follows. Non-adherent cells (U937 monocytes and 293 renal cells) are grown to a concentration of $1 \times 10^6$ cells per ml of media. The cells are pretreated with rhAPC for 16 hours. Staurosporine 1 ug/ml is added for 3 to 3.5 hours. The cells are diluted to $5 \times 10^5$ cells and stained with both anti-annexin V-FITC and propidium iodide as per the Annexin V-FITC Apoptosis Detection Kit (Oncogene Research Products, Boston, Mass.). Fluorescence detection of annexin V staining is done utilizing the Coulter Flow Cytometer (Coulter™).

Significant inhibition of apoptosis by rhAPC is observed in both the U937 cells and the 293 cells.

TABLE 6

Apoptosis Percentage Inhibition in U937 Cells Annexin V Assay

| Treatment | Percent Apoptosis | Std. Error |
|---|---|---|
| Staurosporine (SS) | 100 | 1.88 |
| rhAPC 0.5 ug/ml +SS | 10.9 | 0.46 |
| rhAPC 5.0 ug/ml +SS | 4.2 | 0.84 |

TABLE 7

Apoptosis Percentage Inhibition in 293 Cells Annexin V Assay

| Treatment | Percent Apoptosis | Std. Error |
|---|---|---|
| Staurosporine (SS) | 6.08 | 0.58 |
| rhAPC 0.5 ug/ml +SS | 4.02 | 0.08 |
| rhAPC 5.0 ug/ml +SS | 4.50 | 0.49 |
| rbAPC 10 ug/ml +SS | 4.34 | 0.057 |

EXAMPLE 4

Effect of rhAPC on Adhesion Molecule Expression

The effect of rhAPC on the expression of adhesion molecules ICAM-1, E-selectin, and VCAM-1, is shown in Table 8. HUVEC or Eahy926 endothelial cells grown in T-75 flasks at 80–90% confluence are pretreated with rhAPC (5 ug/ml) for 16 hours and/or Tumor necrosis factor alpha (TNF 1 ng/ml for 7 hours). Expression of the adhesion protein is assessed by flow cytometry. Data for adhesion is compared to TNF average maximal response. The primary antibody at 1–2 ug/ml in 100 uL of FACS buffer (PBS, albumin 5%, sodium azide 0.02%) is applied for 30 min at 4C. The secondary antibody, anti-mouse IgG-FITC, at 1 ug/ml in 100 ul of FACS buffer is applied at 4C for 30 min. FACS analysis is done using a Coulter Flow Cytometer (Coulter™). Primary antibodies were to adhesion markers ICAM-1, E-selectin, and VCAM-1 (R&D Systems, Minneapolis, Minn.). Significant suppression by rhAPC of the expression of ICAM-1 and E-selectin was observed.

TABLE 8

Effect of rhAPC on Adhesion Molecule Expression

| Adhesion Molecule | Average Expression | St Dev. |
|---|---|---|
| ICAM-1 | 0.36 | 0.098 |
| E-selectin | 0.322 | 0.049 |
| VCAM-1 | 0.61 | 0.330 |
| TNFα control | 1.0 | |

EXAMPLE 5

Treatment of Diseases or Pathological Conditions Associated with Apoptosis

This protocol is a controlled trial in patients with multiple sclerosis which displays many hallmarks of apoptosis and is treated with rhAPC or rhAPC derivatives as described herein.

For multiple sclerosis, the attending physician administers rhAPC or an rhAPC derivative subcutaneously at a dose of 0.5 mg/day, to ensure a slower release into the bloodstream. The treatment is continued until the patient is relieved of the symptoms of the disorder.

Another protocol is a controlled trial in patients with Hashimoto's thyroiditis which displays many hallmarks of apoptosis and is treated with rhAPC or rhAPC derivatives as described herein.

For Hashimoto's thyroiditis, the attending physician administers rhAPC or an rhAPC derivative subcutaneously at a dose of 0.5 mg/day, to ensure a slower release into the bloodstream The treatment is continued until the patient is relieved of the symptoms of the disorder.

Yet another protocol is a controlled trial in patients with Graves Disease which displays many hallmarks of apoptosis and is treated with rhAPC or rhAPC derivatives as described herein.

For Graves Disease, the attending physician administers rhAPC or an rhAPC derivative subcutaneously at a dose of 0.5 mg/day, to ensure a slower release into the bloodstream. The treatment is continued until the patient is relieved of the symptoms of the disorder.

An additional treatment protocol is a controlled trial in patients with chronic hepatitis which displays many hallmarks of apoptosis and is treated with rhAPC or rhAPC derivatives as described herein.

For chronic hepatitis, the attending physician administers rhAPC or an rhAPC derivative subcutaneously at a dose of 0.5 mg/day, to ensure a slower release into the bloodstream. The treatment is continued until the patient is relieved of the symptoms of the disorder.

Another protocol is a controlled trial in patients with systemic lupus erythematosus which displays many hallmarks of apoptosis and is treated with rhAPC or rhAPC derivatives as described herein.

For systemic lupus erythematosus, the attending physician administers rhAPC or an rhAPC derivative subcutaneously at a dose of 0.5 mg/day, to ensure a slower release into the bloodstream. The treatment is continued until the patient is relieved of the symptoms of the disorder.

Another protocol is a controlled trial in patients with Alzheimer's disease or Parkinson's disease which displays many hallmarks of apoptosis and is treated with rhAPC or rhAPC derivatives as described herein.

For Alzheimer's disease or Parkinson's disease, the attending physician administers rhAPC or an rhAPC derivative subcutaneously at a dose of 0.5 mg/day, to ensure a slower release into the bloodstream. The treatment is continued until the patient is relieved of the symptoms of the disorder.

For all of the above mentioned treatment protocols, the particular dose of rhAPC or rhAPC derivative administered and the route of administration is adjusted by the attending physician evaluating the particular circumstances surrounding the case, including the compound administered, the particular condition being treated, the patient characteristics and similar considerations.

What is claimed:

1. A method of treating a human patient suffering from a disease or pathological condition selected from the group consisting of inflammatory bowel disease, vasculitis, renal ischemia, and pancreatitis comprising: administering to said patient about 1 µg/kg/hr to about 50 µg/kg/hr of recombinant human activated protein C by continuous infusion for about 1 to about 240 hours.

2. The method according to claim 1 wherein said disease or pathological condition is pancreatitis.

3. The method according to claim 1, wherein said patient is administered about 24 µg/kg/hr of the recombinant human activated protein C.

* * * * *